United States Patent [19]

Sekikawa et al.

[11] Patent Number: 4,548,906

[45] Date of Patent: Oct. 22, 1985

[54] INTEGRAL MULTILAYER ANALYTICAL ELEMENT FOR THE ANALYSIS OF AMMONIA OR AN AMMONIA FORMING SUBSTRATE AND A METHOD FOR THE DETECTION THEREOF USING THE SAME

[75] Inventors: Nobuyoshi Sekikawa; Harumi Katsuyama; Asaji Kondo, all of Asaka, Japan

[73] Assignee: Fuji Shashin Film Kabushiki Kaisha, Japan

[21] Appl. No.: 609,291

[22] Filed: May 11, 1984

Related U.S. Application Data

[63] Continuation of Ser. No. 437,477, Oct. 28, 1982, abandoned.

[30] Foreign Application Priority Data

Nov. 2, 1981 [JP] Japan ................................. 56-176275

[51] Int. Cl.[4] ....................... C12Q 1/58; G01N 33/52; G01N 33/62; G01N 33/70
[52] U.S. Cl. ..................................... 436/113; 422/56; 422/58; 435/12; 435/23; 435/805; 435/807; 436/170
[58] Field of Search ................................... 422/56–58; 436/170, 113; 435/805, 4, 12, 23, 807

[56] References Cited

U.S. PATENT DOCUMENTS

| Re. 30,267 | 5/1980 | Bruschi ................................ 436/170 |
| 3,873,269 | 3/1975 | Kraffczyk et al. ............... 422/56 X |
| 3,992,158 | 11/1976 | Przybylowicz et al. ............. 422/57 |
| 4,223,089 | 9/1980 | Rothe et al. ...................... 422/56 X |

*Primary Examiner*—Arnold Turk
*Attorney, Agent, or Firm*—Jacobs & Jacobs

[57] ABSTRACT

An integral multilayer analytical element for the analysis of ammonia or an ammonia forming substrate in a liquid sample is disclosed. The element comprises a transparent support on which an indicator layer for ammonia, a liquid blocking layer, a reagent layer incorporated with a reagent which may react with the substrate to form ammonia, and a spreading layer, are integrally superposed in this order. The improvement is that the liquid blocking layer is made of a porous material which is permeable to ammonia but substantially impermeable to liquids.

6 Claims, No Drawings

INTEGRAL MULTILAYER ANALYTICAL ELEMENT FOR THE ANALYSIS OF AMMONIA OR AN AMMONIA FORMING SUBSTRATE AND A METHOD FOR THE DETECTION THEREOF USING THE SAME

CROSS-REFERENCE

This is a continuation of Ser. No. 437,477 filed Oct. 28, 1982, now abandoned.

BACKGROUND OF THE INVENTION

1. Field of the Invention

This invention relates to an integral multilayer analytical element for the analysis of ammonia or an ammonia forming substrate in a liquid sample and a method for the detection thereof using the same and more particularly, to an analytical element and a method useful for the analysis of urea nitrogen in body fluids such as blood and urine.

2. Description of the Prior Art

It is very important to determine the concentration of urea nitrogen, ammonia, creatinine and the like in body fluids for the diagnosis and/or the observation of the progress of a certain disease such as a kidney disease. In the past, the analysis of urea nitrogen has been conducted by so-called wet chemistry or solution methods. Such solution methods include a method wherein urea is directly reacted with diacetylmonoxime and the absorbence of the resulting compound is photometrically measured. In addition, there are also other methods wherein urea is reacted with an urease to decompose it into ammonia carbonate and consequently into ammonia which is then reacted with Nessler's reagent to form a colored product or urea is reacted with phenol/hypochlorite to form a colored indophenol, such colored products are colorimetrically measured to determine the amount of urea. Although such methods are useful, they disadvantageously require an expensive equipment, a precise technique, and a long time for the analysis.

In view of such disadvantages of the solution methods, a variety of the so-called dry chemistry methods have recently been proposed in order to carry out the analysis of urea nitrogen simply and rapidly without personal errors. (see, for example, K. Okuda, "Rinsho-Kensa" (Journal of Medical Technology), vol. 22, No. 11, 1203–1218 (1978); Japanese Patent Laid-Open Publication No. 93494/1975 discloses a composition for the quantitative analysis of urea, said composition comprising an enzyme system having an urease activity, a pH indicator, and a barrier-forming body). A typical dry chemistry method uses an integral analytical element comprising a reagent layer containing urease and an alkaline buffer, an indicator layer for the detection of gaseous ammonia, and a selective permeation layer which is interposed between the reagent and the indicator layers and which allows only gaseous ammonia to pass therethrough. For example, Japanese Patent Laid-Open Publication No. 3488/1977 (Corresponding to U.S. Pat. No. Re. 30,267) discloses an integral analytical element having the multilayer structure substantially described above. This analytical element uses a selective permeation layer comprising a polymer membrane for gaseous ammonia. This selective permeation layer has some disadvantages in that the element has low sensitivity due to the low velocity at which the ammonia gas passes through the selective permeation layer. When the thickness of the layer is decreased, the velocity at which the ammonia gas passes through the layer is increased and the element has increased sensitivity, but it becomes impossible to carry out precise analysis because such a thin layer also allows liquid to pass therethrough. In addition, the time for ammonia to diffuse and pass through this membrane changes very much according to its thickness and therefore, it is necessary to make the thickness of the membrane uniform, which requires extremely high techniques. And it is difficult to make adhesion between an aqueous matrix of reagent layer and the selective permeation-layer comprising hydrophobic polymer membrane, which is one of the problems in making such integral analytical element.

On the other hand, Japanese Patent Laid-Open Publication No. 151096/1979 (U.S. Pat. No. 4,223,089) discloses an analytical element in which the defects of the prior art described above, especially the disadvantage of low sensitivity due to long passing time by diffusion, have been improved. In this analytical element, a spacer of woven or knitted net or perforated foil is used as a selective permeation-layer for ammonia gas so that the disadvantage in sensitivity is somewhat improved. However, this element is a nonintegral type and consequently, it is low in sensitivity especially in a low concentration region and unsuitable for the analysis of a sample such as blood which is desired to carry out its analysis with trace amounts thereof. Upon using this element, the reagent layer and the spacer are removed to expose an indicator layer of which change in color is determined. Such operation and handling are troublesome. An analytical device for the analysis of ammonia as illustrated in Example and Drawing of the specification uses absorbent materials such as paper and porous synthetic resin, as a support of an indicator layer. By the method in which color change in the opaque support is photometrically measured, it is impossible to achieve the measurement with which accuracy due to irregular reflection and masking effects on the opaque support. Accordingly, this analytical device may disadvantageously be applied to only semi-quantitative analysis or relatively low accuracy quantitative analysis.

SUMMARY OF THE INVENTION

In view of the disadvantages of the prior analytical elements for the analysis of ammonia or a ammonia forming substrate, the inventors of this invention have conducted studies for an integral multilayer analytical element which has a high sensitivity and a high accuracy and makes simple and convenient analysis in a short time possible and have accomplished this invention. This invention is characterized by providing an air-barrier layer or a liquid blocking layer which allows ammonia gas to pass therethrough but inhibits liquids to pass, between an indicator layer and a reagent layer.

According to this invention there is provided an integral multilayer analytical element for the analysis of ammonia or an ammonia forming substrate in liquid samples, said element comprising a transparent support on which (i) an indicator layer for gaseous ammonia, (ii) a liquid blocking layer, (iii) a reagent layer incorporated with a reagent which may react with the substrate to form ammonia and, (iv) a spreading layer, are integrally superposed in this order, said liquid blocking layer being made of a porous material which comprises such voids that allows gaseous ammonia to pass therethrough but substantially blocks the passage of liquids under conditions of use thereof.

The multilayer analytical element of this invention is useful for the analysis of ammonia itself or for the indirect analysis of an ammonia forming substate which reacts with a reagent to form ammonia which is to be determined with the element. A combination of such ammonia forming substrates with the reagent includes urea/urease, creatinine/creatinine deiminase, amino acid/amino acid dehydrogenase, amino acid/amino acid oxidase, amino acid/amino acid dehydratase, amino acid/ammonialyase, amine/amine-oxidase, diamine/amine-oxidase, glucose and phosphoamidate/-phosphoamidate hexose phospho-transferase, ADP-/carbamate kinase and carbamoyl phosphate, acid amide/amide hydratase, nucleobase/deaminase, nucleotide/deaminase, guanine/guaninase and the like. As mentioned above, the term "ammonia forming substate" used in the specification and the appended claims describes a compound or a group of compounds which directly forms ammonia by the reaction with a specific reagent or which indirectly forms ammonia through plural reaction systems.

Hydrophobic transparent supports which are generally used in such analytical elements and which are made of hydrophobic materials such as polyethylene terephthalate, polycarbonate and polyvinyl compounds, may be used in the analytical element of this invention.

An indicator layer is provided on the support. The indicator layer is incorporated with one or more compounds which change in absorption wavelength as a result of the reaction with gaseous ammonia (which compounds are, hereinafter, referred to as a dye precursor). The dye precursor which may be used in the analytical element of this invention includes leuco dyes such as leucocyanine dye, nitro-substituted leuco dye and leucophthalein dye (see Japanese Patent Laid-Open Publication No. 3488/1977) (Corresponding to U.S. Pat. No. Re. 30,267); pH indicators such as Bromophenol Blue, Bromocresol Green, Bromothymol Blue, Qinoline Blue and rosolic acid (see "Kagaku Dai-Jiten" (Chemical Dictionary) Kyoritsu, vol. 10, 63–65); triarylmethane dye precursors, leucobenzilidene pigments (see the specification of Japanese Patent Application (OPI) No. 145273/1982); diazonium salts and azo dye couplers; base bleachable dyes.

One or more dye precursors above are mixed with organic solvent soluble or water soluble binder and then coated on the transparent support to provide an indicator layer. Binders for this purpose include cellulose esters such as cellulose acetates (mono-, di- and tri-), cellulose acetate butyrate, and cellulose acetate propionate; alkyl cellulose such as methyl cellulose, ethyl cellulose, and propyl cellulose; synthetic vinyl polymers such as polymethylmethacrylate, polyacrylate, polystyrene, polyacrylonitril, polyvinylacetate, polyvinylbutyral, chlorinated polyvinylacetate, polyacrylamide, polyvinylpyrrolidone, polyvinylalcohol, polymaleic acid anhydride, polyolefin and copolymers thereof.

Each binder may be used, according to its solubility or shape, in the form of a homogeneous solution in organic or aqueous solvents, or a latex dispersion in aqueous or organic solvents.

The amount of the dye precursor used may be ranging from 10 to 70% based on the weight of the binder. In order to prevent the dye precursor from coloration during the preparation of the element, organic or inorganic acids such as ethanesulfonic, 3,3-dimethyl glutaric, citric, p-toluenesulfonic, perchloric or hydrochloric acid may be used to adjust the pH to a range within which no color development of the precursor occurs. These liquids containing the dye precursor are added to water or organic solvents such as acetone, Methyl Cellosolve, methyl ethyl ketone, dichloromethane, dichloroethane, methanol or ethanol to prepare a coating liquid containing 1 to 20%, preferably 3 to 10% by weight solids. The coating liquid is coated on the transparent support in dry-thickness of 1 to 20 $\mu$m and dried to give an indicator layer.

On the indicator layer thus formed, a liquid blocking layer is provided.

The liquid blocking layer of the element of this invention comprises a porous substance having voids which are permeable to gaseous ammonia but substantially impermeable to liquids under conditions of use of the element. Preferably, the porous substance is made of hydrophobic or hydrophobicly (water repellently) treated materials in which no substantial capillary action by liquids, especially water, occurs. For example, a membrane filter of cellulose acetate, cellulose nitrate, regenerated cellulose, polyamide, polycarbonate of bisphenol A or polyethylene, or these materials treated with a water repellent if necessary, may advantageously be used. For the purpose of this invention, the thickness of the membrane filter ranges from 30 to 300 $\mu$m, preferably 70–200 $\mu$m and its porosity is above 25%, preferably above 76%. Mean pore size in diameter ranges from 0.01 to 20 $\mu$m, preferably 0.1 to 10 $\mu$m. Such membrane filter may be prepared by, for example, the process as set forth in Japanese Patent Publication No. 21677/1978 or U.S. Pat. No. 3,992,158. Some are readily and commercially available. Examples of them include FM or FR microfilter such as FM 22, FM 30, FM 45, FM 55, FM 80, FM 120, FM 300 and FM 500 (manufactured by FUJI PHOTOFILM Co. Ltd.), SM 11301, SM 11103, SM 11907 and SM 13604 (manufactured by SARTORIUS), FA, FH, LC or LS series such as FALP 14200 and LSWP 14200 (manufactured by MILLIPORE), membrane filter TM, TM-P, TM-A, ultra filter UH, UK and UP (manufactured by TOYOKAGAKU SANGYO), microporous membrane CELLPORE NW-01 and W-01 (manufactured by SEKISUI CHEMICAL INDUSTRY Co.) and metal porous membrane.

These membrane filters may be employed as they are. However, in a case where hydrophilic membrane filter is to be used, it is desired to treat the filter with a water repellent material as previously described so as to substantially inhibit capillary action by liquids, especially water and thereby to improve impermeability to liquids. The water repellent treatment may readily be carried out by the application of conventional water repellents, such as silicone oil, silicone resin, fluorine oil, fluorine plastics and the like, usually diluted with solvents, to membrane filters by dipping, coating, spraying and the like.

The membrane filters may be bonded, with practical adhesive strength, to various materials including water soluble or organic solvent soluble binders which comprise the matrix of the indicator layer. Adhesion is made by putting the membrane filter on the indicator layer which is, if necessary, wetted and drying. The word "wetted" means that there still exists the solvent in which binder is dissolved or that the dried membrane is again wetted by soluble solvent (organic solvent or water) and thus the binder is in swelled, dispersed or dissolved state. In a case where an adhesive binder such as polyvinylacetate is used in the indicator layer, membrane filter may be bonded to the layer by simply putting thereon and pressing it, without wetting the layer.

On the liquid blocking layer, a reagent layer is provided. The reagent layer contains one or more reagents including urease, creatinine deiminase and so on which react with ammonia forming substrate such as urea and creatinine to form ammonia and preferably further contains alkaline buffer which effectively converts the formed ammonia into gaseous ammonia. Such alkaline buffer has suitably pH of 7 to 9.5 and includes, for example, ethylenediaminetetraacetate (EDTA), tris (hydroxymethyl) aminomethane, phosphates. The reagent layer may contain auxiliaries such as wetting agent, binder cross-linking agent (hardner), stabilizing agent, heavy metal ion trapping agent. It is generally preferred that the auxiliaries are contained in the reagent layer. The trapping agent is used to mask heavy metal ions which may inhibit an activity of enzyme. Complexane such as EDTA 2Na, EDTA 4Na, nitrilotriacetic acid (NTA), and diethylenetriamine pentaacetic acid may be used as the trapping agent. These reagents are mixed with water soluble binder such as gelatine to give a coating liquid which is directly coated on the liquid blocking layer to form a reagent layer. During this procedure, although the liquid blocking layer has a number of voids, water contained in the coating solution almost never passes through the liquid blocking layer so that the underlying indicator layer is subjected to no adverse effect. Moreover, the adhesive strength between the two layers is great to the extent that adhesion failure during the processing of the resulting integral analytical element is almost nil. The amount of reagents such as urease used in the reagent layer is from 0.1 to 50%, preferably 2 to 20% based on the weight of binder. The amount of alkaline buffer used is from 0.1 to 10% based on the weight of binder. The amount of heavy metal ion trapping agents used is from 0.5 to 20% based on the weight of binder. The thickness of the reagent layer is generally from 1 to 20 $\mu$m, preferably 3 to 10 $\mu$m.

A spreading layer is provided on the reagent layer thus formed. If necessary, a light reflection layer is provided. The light reflection layer may be prepared by, for example, coating an aqueous liquid containing titanium dioxide, gelatine, surface-active agent and the like in dry thickness of 0.5 to 20 $\mu$m on the reagent layer and then drying. The spreading layer functions to spread rapidly and radially the liquid sample spotted, then to penetrate it therethrough and finally to distribute the liquid sample uniformly into the reagent layer. The spreading layer used in this invention is any one of the those having the function described above. For example, hydrophilized woven fabric set forth in U.S. Pat. No. 4,292,272 (The term "hydrophilized woven fabric" hereinunder means hydrophilic fabrics made by the process as set forth in U.S. Pat. No. 4,292,272 (column 5 to 6) or the like) and non-fibrous porous medium set forth in Japanese Patent Publication No. 21677/1978 or U.S. Pat. No. 3,992,158 are suitable. When the hydrophilized woven fabric of U.S. Pat. No. 4,292,272 is used, it is preferred to provide previously an adhesive layer containing binder such as gelatine and surface active agent, on the reagent layer or the light reflection layer.

Instead of direct coating of the reagent, light reflection, adhesive and spreading layers on the liquid blocking layer as described above, the four layers are laminated to prepare a multilayer component and then, the reagent layer of the component is laminated with liquid blocking layer by adhesive material to prepare an analytical element.

Adhesive material may be provided by coating an aqueous liquid containing a surface active agent and a latex of copolymer of an acrylic ester, an methacrylic ester and an acrylamide derivative in dry thickness of 0.1 to 5 $\mu$m, preferably 0.5 to 2 $\mu$m and then drying.

Analyzing ammonia or an ammonia forming substrate using the integral multilayer analytical element of this invention, 5 to 30 $\mu$l of sample liquid is spotted on the spreading layer and, if necessary, after incubation at 30° to 40° C., preferably 35° to 39° C. for 1 to 20 minutes, preferably 3 to 10 minutes, the change in color (color development or fading) of the indicator layer may be determined by the light reflection or may be visually compared with the standard through the transparent support.

The integral multilayer analytical element of this invention has a high diffusion rate of ammonia gas because of the liquid blocking layer which constitutes an air layer and therefore, the element requires remarkably shorter time for analysis and has very high accuracy in analysis. Moreover, since the element is an integral type, it is simple and easy to use or handle the element. Commercially available membrane filter itself, or if necessary after water repellent treatment, may be used as a liquid blocking layer of the integral multilayer analytical element of this invention and therefore, the element may be efficiently and economically manufactured by a practical production technique comprising coating and laminating steps suitable for mass production.

This invention will now be concretely described with reference to the following examples to which this invention should not be limited.

EXAMPLE 1

The following illustrates the preparation of an integral multilayer analytical element for the quantitative analysis of blood urea nitrogen.

(1) Indicator layer

On a transparent film base of polyethyleneterephthalate, was coated per one square meter, a solution consisting of:

| Dye precursor: | 4-[bis-(2,4-dinitrophenyl) methyl]-N—hexadecylpyridinium perchlorate | 1.00 g |
|---|---|---|
| Cellulose acetate | | 8 g |
| Acetone | | 65 ml |
| Methyl Cellosolve | | 35 ml |
| Ethanesulfonic Acid | | 25 $\mu$l |

(2) Liquid Blocking Layer

A membrane filter (FUJI MICRO FILTER, FM 500: 140 $\mu$m in thickness, 75% of porosity, 5 $\mu$m of a mean pore size in diameter) was dipped in a solution of silicone resin in hexane and dried. The filter thus treated was superposed on the indicator layer prepared in step 1) while the solvent still remained in the indicator layer (that is, in "wetted" state), which was then dried to give a liquid blocking layer.

(3) Reagent Layer

On the membrane filter, a solution which was adjusted to pH 8 by disodium orthophosphate and sodium hydroxide was coated and dried, the solution consisting of:

| Gelatin | 10 g |
|---|---|
| Water | 100 ml |
| p-Nonylphenoxypolyglycidol | 0.3 g |
| Urease | 0.8 g |
| Ethylenediamine tetraacetic acid tetrasodium salt (EDTA 4 Na) | 0.4 g |

(4) Light Reflection Layer

On the reagent layer, a solution was coated and dried, the solution consisting of:

| $TiO_2$ fine powder | 4 g |
|---|---|
| Gelatin | 4 g |
| p-Nonylphenoxypolyglycidol | 0.15 g |
| Water | 40 ml |

(5) Adhesive Layer

On the light reflection layer, a solution was coated and dried, the solution consisting of:

| Gelatin | 2.5 g |
|---|---|
| Water | 50 ml |
| p-Nonylphenoxypolyglycidol | 0.15 g | so as to combine a spreading layer to the light reflection layer.

(6) Spreading Layer

After the dried surface of the adhesive layer was swollen by water, a piece of cloth (cotton broad #100) for a spreading layer was laminated to form an analytical element.

The analytical elements thus prepared were evaluated by the following method. Aqueous solutions containing 0 to 100 mg of urea nitrogen (UN) per one decilitre of 7% albumin solution were prepared. Each solution (10 μm) was spotted on the spreading layer of the analytical elements. After incubation at 37° C. for 6 minutes, the formed color density at 600 nm was measured on a reflection spectrophotometer through PET film.

The results are shown in the following table.

| Urea Nitrogen (mg/dl) | Reflection Density |
|---|---|
| 0 | 0.16 |
| 4 | 0.25 |
| 12 | 0.50 |
| 25 | 0.95 |
| 50 | 1.74 |
| 75 | 2.26 |
| 100 | 2.40 |

Thus, an analytical element having high sensitivity was obtained.

EXAMPLE 2

The following example was conducted to compare the performance of the integral multilayer analytical element for the detection of blood urea nitrogen of this invention in which a membrane filter is used as a liquid blocking layer, with the performance of the integral multilayer analytical element as set forth in Japanese Patent Laid-Open Publication No. 3488/1977 (Corresponding to U.S. Pat. No. Re. 30,267) in which a polymer membrane (or a barrier layer) of cellulose acetate butyrate is used as a selective permeation layer.

(1) Indicator Layer

A solution consisting of:

| Dye precursor: | 4-[bis(2,4-dinitrophenyl) methyl]-N—hexadecylpyridinium perchlorate | 1.00 g |
|---|---|---|
| Celluose acetate butyrate | | 6 g |
| Methyl ethyl ketone | | 80 ml |
| Dichloro methane | | 20 ml |
| Ethanesulfonic acid | | 50 μl | was coated on a transparent PET film support per square meter.

(2) A membrane filter treated with a silicone water repellent in the similar manner to Example 1 (140 μm thick, 75% porosity, 5 μm mean pore diameter, manufactured by FUJI PHOTO FILM CO., LTD.) was adhered to the one specimen thus prepared in the wetted state. On the other specimen, a 6% solution of cellulose acetate butyrate (CAB) in methyl ethyl ketone (MEK)-dichloromethane was coated to prepare a 1 to 2 μm thick barrier layer (of a selective permeation-layer).

On each coating, as described in Example 1, (3) Reagent Layer, (4) Light Reflection Layer, and (5) Adhesive Layer were in turn coated and dried, then (6) Spreading Layer was placed to form two kinds of analytical elements.

By the method similar to Example 1, the performance of the one element was evaluated in comparison with that of the other element.

| Urea Nitrogen (mg/dl) | Reflection Density | |
|---|---|---|
| | Liquid Blocking Layer (Membrane Filter) | Barrier Layer (CAB membrane) |
| 0 | 0.15 | 0.20 |
| 4 | 0.30 | 0.25 |
| 12 | 0.63 | 0.40 |
| 25 | 1.15 | 0.64 |
| 50 | 1.88 | 1.05 |
| 75 | 2.23 | 1.47 |
| 100 | 2.39 | 1.80 |

From the above, it is apparent that the analytical element using a membrane filter according to the invention is of higher sensitivity than the element using a barrier layer (CAB membrane).

EXAMPLE 3

The procedure of Example 1 was repeated to prepare an integral multilayer analytical element for the quantitative analysis of blood urea nitrogen, except that 1.00 g of Bromophenol Blue was used as a dye precursor.

The element thus prepared was evaluated by the same method as in Example 1 to give the following results.

| Urea Nitrogen (mg/dl) | Reflection Density |
| --- | --- |
| 0 | 0.15 |
| 4 | 0.35 |
| 12 | 0.65 |
| 25 | 1.20 |
| 50 | 1.64 |
| 75 | 1.90 |
| 100 | 2.02 |

EXAMPLE 4

Bromothymol Blue (20 mg) as an indicator was mixed with 4 g of 5% methylcellulose aqueous solution.

The pH of the mixture was adjusted to 4.9 with a sodium hydroxide aqueous solution to give a coating liquid.

The coating liquid thus prepared was coated on a transparent PET support to form a coating of 5 μm in dry thickness. The coated support was then dipped in a 0.2% p-nonylphenoxypolyglycidol aqueous solution at +5° C. and was pressed between silicone rubber rolls adjusted to +5° C. to remove excess liquid therefrom, on which membrane filter similar to Example 1 was pressed to be adhered. As described in Example 1, a reagent, an adhesive and a spreading layers were laminated in turn to form an integral multilayer analytical element for the urea analysis.

Using a similar method to Example 1, the color density corresponding to the quantity of urea nitrogen was observed.

| Urea Nitrogen (mg/dl) | Reflection Density |
| --- | --- |
| 0 | 0.22 |
| 5 | 0.34 |
| 10 | 0.55 |
| 25 | 1.06 |
| 45 | 1.64 |
| 75 | 2.05 |
| 100 | 2.14 |

EXAMPLE 5

A coating liquid consisting of:

| | |
| --- | --- |
| Bromocresol Green | 60 mg |
| Latex of Copolymer of vinyl acetate and acrylic ester (about 50% solid, pH 4.4) | 5 g |
| 3,3-Dimethylglutaric acid | 20 mg |
| Water | 2 ml | was coated as an indicator layer on a transparent PET film to give a coating of 10 μm in dry thickness. On dried and adhesive indicator layer thus prepared, a membrane filter as described in Example 1 was pressed by a laminator. Then, in a similar manner to Example 1, a reagent, an adhesive and a spreading layers were closely laminated in turn to prepare an integral multilayer analytical element for the urea analysis.

By the same method as that described in Example 1, the reflection density corresponding to each quantity of urea nitrogen contained in commercially available control serum and in urea added samples was observed.

| Urea Nitrogen* (mg/dl) | Reflection Density |
| --- | --- |
| 0 | 0.13 |
| 15 | 0.60 |
| 23 | 0.81 |
| 40 | 1.29 |
| 52 | 1.55 |
| 95 | 2.02 |
| 115 | 2.17 |

*A physiological saline solution containing 7% albumin was used.

EXAMPLE 6

A mixture of

| | |
| --- | --- |
| Glyoxal | 2.5 mg |
| Bromocresol Green | 20 mg |
| 5% Methylcellulose aqueous solution | 5 g | was coated, as an indicator layer, on a transparent, photographic PET film precoated with agarose to give a coating of 3 μm in dry thickness.

On the indicator layer, a membrane filter (FUJI Micro Filter FM 80, 0.8 μm pore in diameter) treated with a silicone resin solution in a manner identical with that described in Example 4 was laminated.

On the multilayer film above, a coating liquid consisting of:

| | |
| --- | --- |
| Deionized gelatin | 10 g |
| Creatinine deiminase | 3000 units |
| N—tris(hydroxymethyl)methyl-2-aminoethanesulfonic acid-phosphoric acid | 0.07 g |
| KH$_2$PO$_4$ | 0.08 g |
| Boric acid | 2.5 g |
| Alkylallyl polyethersulfonic acid sodium salt | 0.06 g |
| Water | 150 g | was coated to give a reagent layer.

Then, an adhesive layer and a spreading layer of cotton broad were in turn laminated to prepare an analytical film for the creatinine analysis.

On the spreading layer, 10 μl of each sample was spotted and incubated at 37° C. for 3 minutes. The color density was measured at 600 nm by a reflection spectrophotometer.

| Creatinine (mg/dl) | Reflection Density |
| --- | --- |
| 0.05 | 0.17 |
| 1.0 | 0.20 |
| 2.0 | 0.24 |
| 5.0 | 0.40 |
| 10.0 | 0.90 |
| 16.0 | 1.63 |

EXAMPLE 7

The procedure of Example 6 was repeated to prepare an analytical film for the detection of creatinine, except that Bromophenol Blue was employed as an indicator.

| Creatinine (mg/dl) | Reflection Density |
| --- | --- |
| 0.05 | 0.22 |
| 1.0 | 0.26 |
| 2.0 | 0.37 |
| 5.0 | 0.64 |
| 10.0 | 1.13 |
| 15.0 | 1.62 |

EXAMPLE 8

An indicator layer similar to that described in Example 5 was coated on a PET film. On the adhesive indicator layer after dried, a membrane filter without water repellent treatment was pressed by a laminator.

A reagent, a light reflection, an adhesive and a spreading layers similar to those described in Example 1 were in turn coated or laminated on another PET film having good releasability to give a multilayer component. After removing the PET film, the multilayer component was laminated with the membrane filter above through an adhesive (a latex of copolymer of 85 mole % of butyl acrylate, 5 mole % of 2-acetoacetoxyethyl methacrylate and 10 mole % of N-(2-sulfo-t-butyl)acrylamide to prepare an analytical element.

The element thus prepared was evaluated by a method similar to that described in Example 1 to give the following results.

| Urea Nitrogen (mg/dl) | Reflection Density |
| --- | --- |
| 0 | 0.21 |
| 15 | 0.51 |
| 34 | 0.90 |
| 42 | 1.03 |
| 58 | 1.37 |
| 76 | 1.64 |
| 98 | 1.96 |

What we claim is:

1. An integral multilayer analytical element for the analysis of ammonia or an ammonia forming substrate in a liquid sample, said element comprising a transparent support including thereon integrally superposed from the support upward (i) an indicator layer for gaseous ammonia, said indicator layer being visible through said transparent support, (ii) a membrane filter as a liquid blocking layer, said membrane filter being composed of a porous material having voids which are permeable to gaseous ammonia but substantially impermeable to liquid under conditions of use thereof, said porous material being a hydrophobic or hydrophobed material in which no substantial capillary action by water occurs, and said membrane filter being 30 to 300 $\mu$m in thickness, having a porosity of more than 25% and a mean pore diameter of from 0.01 to 20 $\mu$m, (iii) a reagent layer comprising a water soluble binder and a reagent which may react with the substrate to form ammonia and (iv) a spreading layer, the adhesive strength between said membrane filter and said reagent layer being sufficient to provide an integral unit.

2. The analytical element as defined in claim 1 wherein said ammonia forming substrate is urea and said reagent which reacts with said substrate to form ammonia is urease.

3. The analytical element as defined in claim 1 wherein said ammonia forming substrate is creatinine and said reagent which reacts with said substrate to form ammonia is creatinine deiminase.

4. The analytical element as defined in claim 1 wherein said reagent layer further includes a stabilizer and a surface active agent.

5. The analytical element as defined in claim 1 wherein said indicator layer includes a dye precursor which forms a dye in the presence of ammonia.

6. A method for the detection of ammonia or an ammonia forming substrate in a liquid sample, which comprises:

providing an integral multilayer analytical element for the analysis of ammonia or the ammonia forming substrate, said element comprising a transparent support including thereon integrally superposed from the support upward (i) an indicator layer for gaseous ammonia, said indicator layer being visible through said transparent support, (ii) a membrane filter as a liquid blocking layer, said membrane filter being composed of a porous material having voids which are permeable to gaseous ammonia but substantially impermeable to liquid under conditions of use thereof, said porous material being a hydrophobic or hydrophobed material in which no substantial capillary action by water occurs, and said membrane filter being 30 to 300 $\mu$m in thickness, having a porosity of more than 25% and a pore diameter of from 0.01 to 20 $\mu$m, (iii) a reagent layer comprising a water soluble binder and a reagent which may react with the substrate to form ammonia and, (iv) a spreading layer, the adhesive strength between said membrane filter and said reagent layer being sufficient to provide an integral unit, spotting said sample on said spreading layer of said element, and measuring visually or photometrically through the transparent support the development or fading of color in the indicator layer resulting from the reaction between the indicator and ammonia which was formed in the reagent layer and passed through the liquid blocking layer.

* * * * *